United States Patent [19]
Leone

[11] Patent Number: 5,709,653
[45] Date of Patent: Jan. 20, 1998

[54] PHOTODYNAMIC THERAPY BALLOON CATHETER WITH MICROPOROUS MEMBRANE

[75] Inventor: James E. Leone, Miami, Fla.

[73] Assignee: Cordis Corporation, Miami Lakes, Fla.

[21] Appl. No.: 690,330

[22] Filed: Jul. 25, 1996

[51] Int. Cl.[6] .................................................. A61N 1/30
[52] U.S. Cl. ............................. 604/20; 604/49; 604/96; 606/15; 606/16
[58] Field of Search ............................ 604/19–21, 49, 604/96; 606/7–8, 13–17; 607/80, 88–89; 128/633, 634

[56] References Cited

U.S. PATENT DOCUMENTS

| | | |
|---|---|---|
| 4,636,195 | 1/1987 | Wolinsky . |
| 4,878,492 | 11/1989 | Sunofsky et al. ........................ 606/7 |
| 5,047,028 | 9/1991 | Qian . |
| 5,049,132 | 9/1991 | Shaffer et al. . |
| 5,087,243 | 2/1992 | Avitall . |
| 5,092,841 | 3/1992 | Spears ........................ 604/96 |
| 5,169,395 | 12/1992 | Narciso, Jr. ........................ 606/14 |
| 5,213,576 | 5/1993 | Abiuso et al. . |
| 5,236,413 | 8/1993 | Feiring . |
| 5,286,254 | 2/1994 | Shapland et al. . |
| 5,303,324 | 4/1994 | Lundahl ........................ 606/7 |
| 5,318,531 | 6/1994 | Leone . |
| 5,405,472 | 4/1995 | Leone . |
| 5,505,700 | 4/1996 | Leone et al. . |
| 5,634,946 | 6/1997 | Slepian ........................ 623/11 |

FOREIGN PATENT DOCUMENTS

| | | |
|---|---|---|
| 2154761 | 9/1985 | Georgia . |
| 9000914 | 2/1990 | WIPO . |
| 9116945 | 11/1991 | WIPO . |
| 9119529 | 12/1991 | WIPO . |

Primary Examiner—Mark Bockelman
Assistant Examiner—Ellen Tao
Attorney, Agent, or Firm—Lockwood, Alex, Fitzgibbon & Cummings

[57] ABSTRACT

A photodynamic therapy balloon catheter with microporous membrane is provided which has an elongated optical fiber, an inner tubular member, a porous balloon member surrounding the inner tubular member, and fluid material provided between the inner tubular member and the porous balloon member. The porous balloon member having a plurality of holes of a size to permit medication delivered through a lumen to pass outwardly through the holes. The balloon carries on an outer surface a substantially hydrophilic, tubular microporous membrane covering the holes, to break up streams of flowing medication. Light-reflective material is included in any one of a plurality of the inner member, fluid material, porous balloon member, and microporous membrane in any combination to provide a uniform light illumination for activating treatment fluids located on an elongated treatment site within a living body.

44 Claims, 3 Drawing Sheets

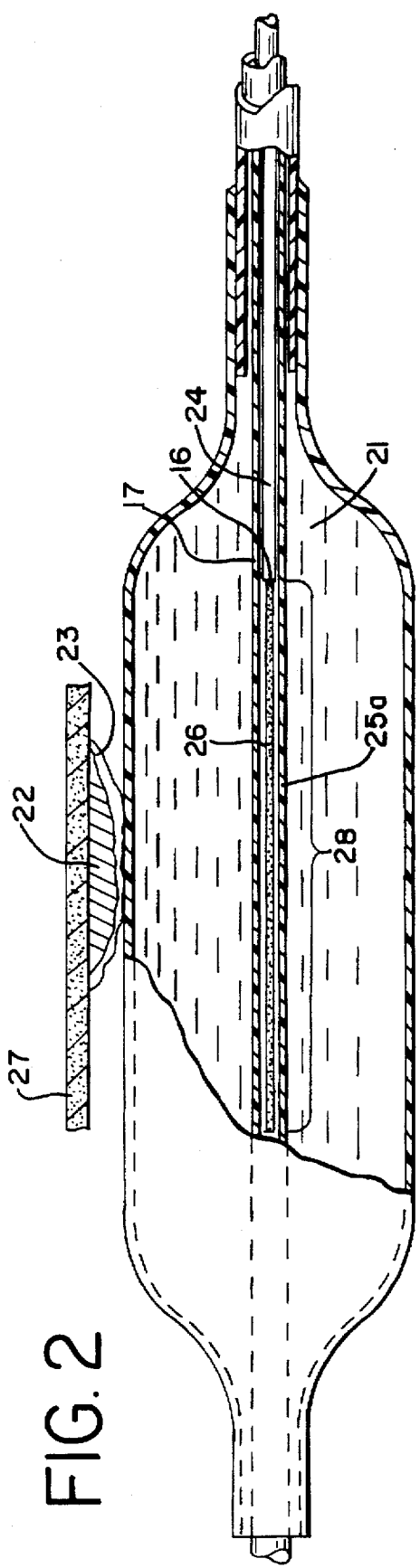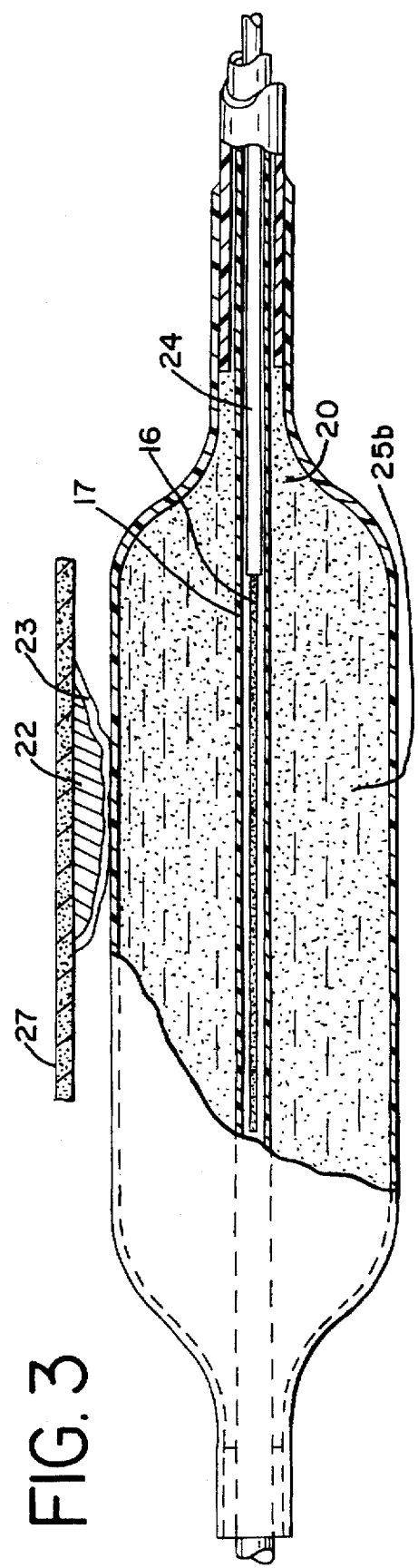

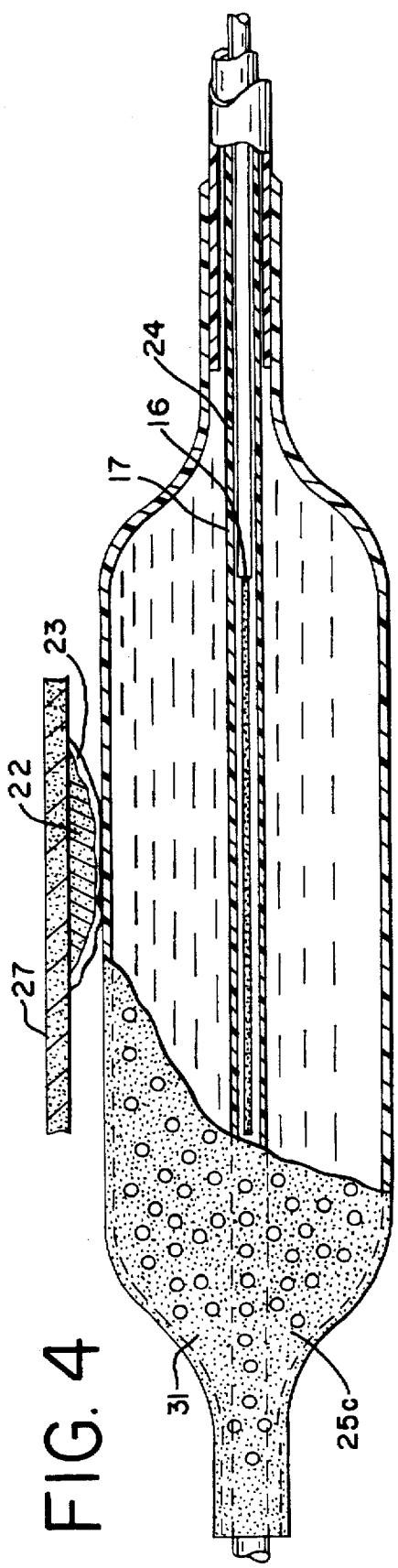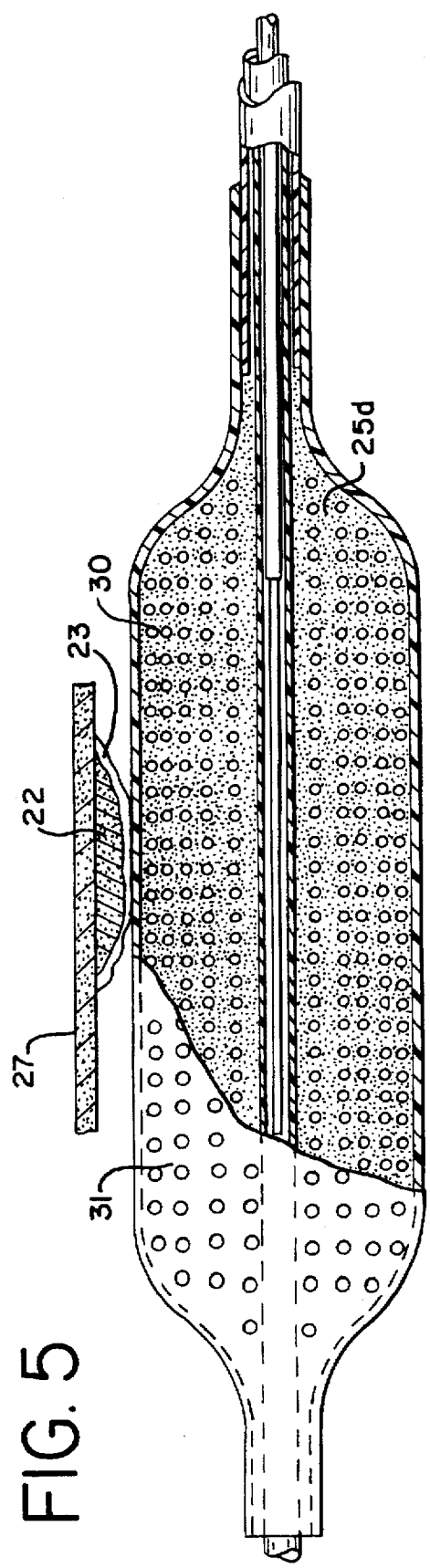

PHOTODYNAMIC THERAPY BALLOON CATHETER WITH MICROPOROUS MEMBRANE

DESCRIPTION

BACKGROUND AND SUMMARY OF THE INVENTION

The present invention generally relates to medical catheters for activation of treatment fluids or medicaments at treatment sites within a living body. More particularly, the invention relates to photodynamic therapy balloon catheters which have optical features which more uniformly apply light energy in activating the treatment fluid at an in vivo treatment location.

Medicaments can be administered to living bodies by a number of approaches, including topical administration, intravenous administration, injection into body tissue via hypodermic needles and the like, and oral administration. In some instances, it is important to minimize the contact of the medicament with areas of the body other than the specific area targeted for treatment. For example, such an approach reduces the dilution effect by having to distribute the medicament to portions of the body that do not require the treatment. Direct delivery to the target site also minimizes the chance of side effects by restricting the drug administration to the precise site in need of treatment. In other instances, the area to be treated is not readily accessible in the absence of fully invasive surgery, such as when it is desired to treat the interior of a blood vessel or other body vessel or cavity.

Over the years, photodynamic catheters have been developed in order to provide for the activation of treatment fluids, medication, pharmaceuticals, drugs or other medicaments at a localized site. These are photodynamic components, and they do not become fully activated until they are illuminated with a prescribed light source, as generally known in the photodynamic medication art. This illumination must be of the inside of the vessel at the site being treated. Thus, photodynamic catheters have been proposed.

One difficulty that has been encountered in connection with photodynamic catheters for delivering the needed lumination is the lack of uniformity of light illuminating and activating the treatment fluids. In many photodynamic catheters, light is provided through an optical fiber to the distal end of the catheter. Typically this light is focussed or in a narrow or directed beam or beams, which can cause "hot spots" in the blood vessel or other internal organs. The "hot spots" typically result in uneven activation of the treatment fluid.

More particularly, photodynamic catheters can utilize optical fibers to provide light energy at the treatment site where the treatment fluid has been infused. A substantial shortcoming of these types of catheters can be the uneven illumination of the treatment fluid. As the photodynamic catheter is inserted through the body and positioned adjacent to the treatment site, the optical fiber transmits and provides a narrow beam of light at the treatment site through its distal tip. Since an optical fiber has cladding around its core, the light is directed through its length to its tip section. As the narrow beam of light emanates from the tip section of the optical fiber, it is more concentrated and longitudinally directed. Since the light emanates from the tip of the optical fiber and is longitudinally directed, it does not radiate efficiently in a radial direction perpendicular to the longitudinal axis of the optical fiber.

Moreover, since the tip of the optical fiber has a light emanating surface which is relatively short in the longitudinal direction, it does not illuminate simultaneously the entire surface area of the treatment fluid along the length of an elongated treatment location. As a result, different portions of the surface of the treatment fluid can be illuminated for different lengths of time, causing non-uniform activation of the photodynamic treatment fluid or medication. An approach which could be used to address this problem is to maneuver the photodynamic catheter in a forward and/or reverse direction, along the length of the treatment location, with a constant speed so that all of the photodynamic treatment fluid is illuminated with a same amount of light energy and for a same amount of time, providing a more even illumination of the entire surface of the treatment fluid. Such a maneuvering requirement becomes an additional variable which can detrimentally affect the reliability of the photodynamic catheterization procedure.

In accordance with this invention a balloon catheter is provided which has a catheter shaft assembly having an inner member and at least one balloon carried on the shaft assembly and over the inner member. An optical fiber is positioned inside the inner member. A lumen of the shaft assembly communicates between a space located within the balloon and a proximal end portion of the shaft assembly, and provides for the delivery of medication and fluid material. The balloon has a plurality of holes which are of a size to permit medication delivered through the holes to pass outwardly through the holes. The balloon also has an outer surface, which outer surface carries a tubular, substantially hydrophilic, microporous membrane covering the holes of the balloon, to break up streams of flowing medication. Moreover, reflective material can be included in any one or a plurality of the inner member, porous balloon member, fluid material, and microporous membrane in any combination. By adding the reflective material in these different combinations, it is possible to provide for the uniformity of light illumination for activating any of various photodynamic medicaments and the like.

In accordance with the present invention, the undesirable aspects of "hot spots" and non-uniform light illumination of the treatment fluid is substantially eliminated. Instead, the light illumination of the treatment fluids is rendered uniform through the treatment length achieved by the present invention.

In summary, the present invention is a photodynamic therapy balloon catheter and procedure, wherein the catheter includes an optical fiber having an elongated light-emanating section cylindrically surrounded by a light-passing inner tubular member, a light-passing fluid material, a light-passing inflatable porous balloon member and a microporous membrane, and wherein at least one of the inner tubular member, fluid material, balloon member and/or microporous membrane includes light-reflection material which upon light emanating from the elongated light source of the optical fiber, provides a uniform illumination for activating treatment of photodynamic fluids delivered at blood vessel walls or other internal organs through the porous balloon and microporous membrane.

It is a general object of the present invention to provide an improved photodynamic therapy balloon catheter and method of using same.

Another object of the present invention is to provide an improved photodynamic therapy balloon catheter that carries out localized treatment of internal body tissues.

Another object of this invention is to provide an improved photodynamic therapy balloon catheter which delivers photodynamic treatment fluids and uses uniform light to illuminate the treatment fluids thus delivered to the blood vessel or other internal organs.

Another object of the present invention is to provide an improved photodynamic therapy balloon catheter and procedure using optical principles to provide uniform light energy to treatment fluids at locations within the living body that are accessible through catheterization procedures.

Another object of the present invention is to provide an improved catheter and procedure which carries out localized treatment of internal body tissue, such as re-stenosis reduction and the treatment of cancers by localized activation of the treatment fluids at a tumor location for example.

BRIEF DESCRIPTION OF THE DRAWINGS

The invention will be further elucidated in the following description with reference to the drawings in which:

FIG. 2 is a detailed view shown in cross-section of the first embodiment of the catheter of this invention, illustrating the distal portion of the catheter shown in FIG. 1, located within a body vessel;

FIG. 3 is a detailed view shown in cross-section of the second embodiment of the catheter of this invention, illustrating the distal portion of the catheter shown in FIG. 1, located within a body vessel;

FIG. 4 is a detailed view shown in cross-section of the third embodiment of the catheter of this invention, illustrating the distal portion of the catheter shown in FIG. 1, located within a body vessel; and FIG. 5 is a detailed view shown in cross-section of the fourth embodiment of the catheter of this invention, illustrating the distal portion of the catheter shown in FIG. 1, located within a body vessel.

DESCRIPTION OF THE PARTICULAR EMBODIMENTS

Figure 1:
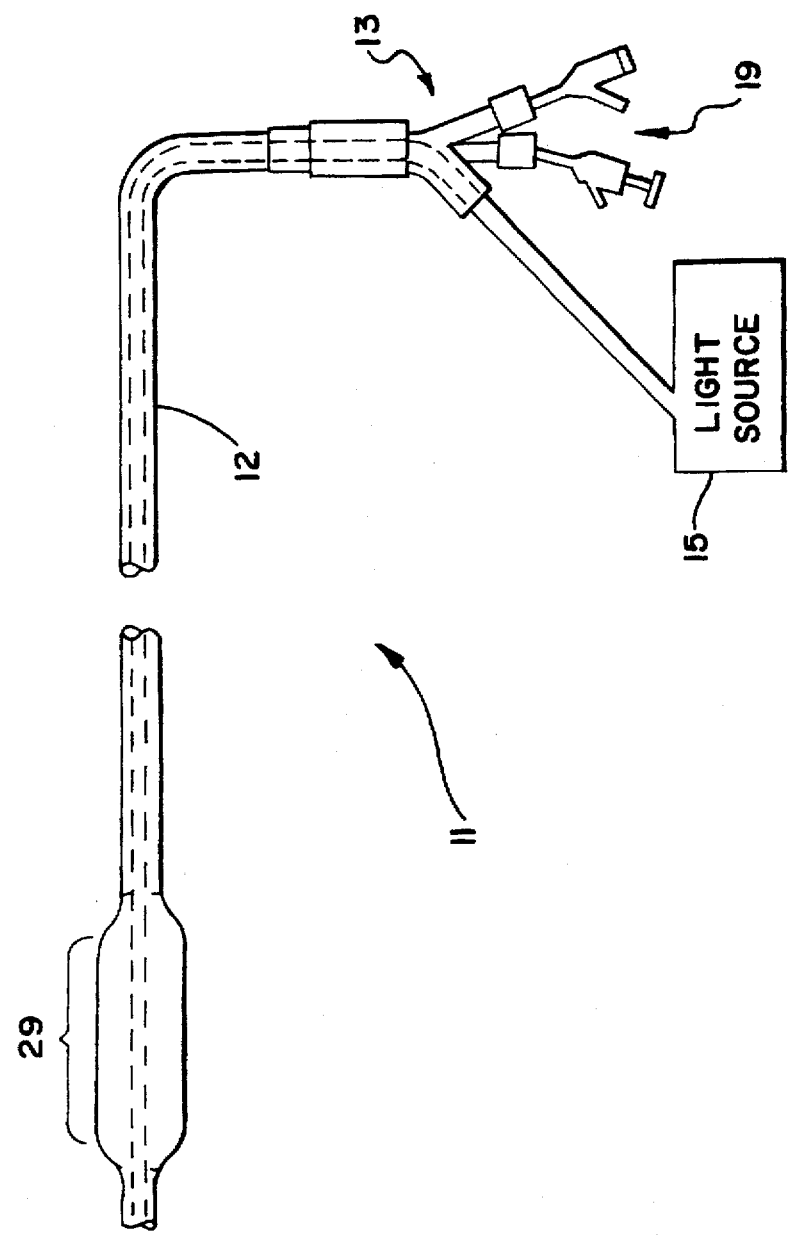
FIG. 1 is an elevational view, partially broken away, of a preferred photodynamic balloon therapy catheter in accordance with the present invention.

A photodynamic therapy balloon catheter, generally designated as 11, is generally illustrated in FIG. 1. The catheter includes a multilumen catheter tube 12, a proximal portion, generally designated as 13, and a distal portion generally designated as 14. Also included is a light transmission system including a light source 15.

As shown in FIG. 2, distal portion 14 includes an optical fiber 16. The optical fiber 16 is positioned interior to an inner tubular member 17. The inner member 17 is generally light-passing or optically clear. Typically, inner member 17 will be made of a biocompatible polymer. Examples include polyamides, polyurethanes, polyesters, polyolefins and the like. More specific examples include nylons, polyethylene, and the like. Suitable nylons include nylon 12, nylon 11, other nylon homopolymers and copolymers with other components. Grilamid (trademark) nylons are specific examples.

The inner member 17 is cylindrically surrounded by a generally light-passing inflatable porous balloon member 18. The porous balloon member 18 is in fluid-passing communication with a lumen within the catheter tube. The porous balloon member 18 is also made of a biocompatible polymer, and typically can be made of polymers of the type used in manufacturing the inner member 17.

A microporous membrane 30 cylindrically surrounds the outer surface of the porous balloon member 18. It will be appreciated that, with the porous balloon member 18 inflated as illustrated in FIG. 5, an annular chamber 21 is defined between the inner member 17 and the porous balloon member 18. A photodynamic treatment fluid 23, with the aid of fluid injector assembly 19 passes through the lumen, and enters the annular chamber 21 causing porous balloon member 18 and the microporous membrane 30 to inflate so that the microporous membrane 30 contacts the vessel wall 27. The treatment fluid 23 passes through the holes 31 of the porous balloon member 18 and the micropores of the microporous membrane 30, and infuses into the diseased area 22.

Typically, subsequent to the passing of the treatment fluid 23 into the annular chamber 21 and its infusion into the diseased area 22, the annular chamber 21 is filled with generally light passing or optically clear fluid material 20 such as saline solution or water. In any event, once the treatment fluid is infused into or about the diseased area, it is then illuminated with light. Upon illumination of the photodynamic treatment fluid, it is activated so that it would provide an optimal effect on treating the diseased area.

Preferably, the substantially hydrophilic, microporous membrane is the outermost member of the balloon catheter, surrounding the single balloon. The balloon defines a generally cylindrical portion. The tubular, microporous membrane is preferably carried by the cylindrical portion of the balloon.

It is generally preferred for the micropores of the membrane to be smaller and more numerous than the holes of the balloon. For example, the micropores of the membrane may be essentially from 0.4 to 3 microns in diameter, while the holes of the balloon are typically, from 5 to 100 microns in diameter. Also, the typical number of the micropores per square centimeter of membrane may be from about one hundred thousand to five hundred million, while the number of the holes in the balloon may be essentially from twenty to one thousand. Also, the microporous membrane may be coated with a hydrophilic agent such as polyvinylpyrrolidone to improve the penetrability of medications through the micropores of the microporous membrane.

The microporous membrane may, for example, be a polycarbonate membrane manufactured by The Poretics Company specifically their TRACK-ETCH PCTE membrane filters, which are manufactured by exposing thin polycarbonate film to collimated, charged particles in a nuclear reactor. Then, the tracks left by the particles are preferentially etched to form uniform, cylindrical pores of predetermined pore size.

Specifically, one suitable hydrophilic, microporous membrane is a TRACK-ETCH PCTE membrane having a pore size of about 0.8 micron and a pore density of about thirty million pores per square centimeter. Such a membrane weighs about 1 milligram per square centimeter, having a thickness of about 9 microns and a water bubble point of about 18 p.s.i. Typically flow rates of water through such a membrane are about 215 ml. per minute per $cm^2$, using prefiltered water at 10 p.s.i. The above data comes from the manufacturer of the polycarbonate screen membrane.

The catheter of this invention may be a standard catheter for intravenous usage such as a PTCA dilatation catheter of low profile, in which the balloon has been perforated with holes having a diameter of approximately 20 to 30 microns (nominally 25 microns). In one embodiment, 64 of such 25 micron holes are present in a balloon catheter which is about 20 millimeters in length and having a diameter of, typically, 2 to 4 millimeters (inflated). Such a balloon may be carried upon an otherwise conventional PTCA catheter having a useable length of 135 cm., and a catheter shaft diameter of 4.0 French or smaller. A guide wire may be used having a diameter of 0.018 millimeter, and the tip length of the catheter may be about 0.2 inch. The balloon may be made of 75 Shore D nylon.

According to the present invention, in order to activate a photodynamic treatment fluid 23, (discussed in greater detail herein) more effectively, it must be illuminated more evenly and uniformly. To uniformly and efficiently illuminate the photodynamic treatment fluid 23, cladding material 24 on the optical fiber 16 is removed at its distal portion, exposing an optical fiber core 26. By removing cladding material 24, an elongated light emanating area 28 is provided. The length of area 28 approximates the working length 29 of balloon member 18. The illuminating light from the elongated light-emanating area 28 radiates in a perpendicular or radial direction in relation to the longitudinal axis of the optical fiber core 26. This perpendicular or radial radiation of the illuminating light provides a cylindrical illumination pattern extending over the working area 29 of the balloon and the entire surface area of the treatment fluid 23, including its entire longitudinal extent.

Furthermore, in order to achieve an even more uniformly lit area, the optical fiber core 26 can be tapered such that it has a reducing thickness in the distal direction. Alternatively, any cladding remaining in the elongated area 28 could be tapered in the same direction. A gradient reduction in the thickness of the optical fiber component provides for the light which emanates along the length of the elongated light-emanating area 28 to illuminate with a higher degree of uniformity. The intensity of the light energy present in the optical fiber core 26 decreases in the distal direction, due to the greater longitudinal distance through which the light must pass at the more distal portions of the optical fiber. By the tapering effect and the reduction in the thickness in the distal direction, the more distal portions have a shorter radial distance through which to pass. Thus, the greater longitudinal distances are combined with the shorter radial distances, and vice versa, to achieve a total light path (longitudinal plus radial) which is about the same throughout the light-emanating area, which allows the light energy emanating from the core 26 to be more uniform.

When included, the tapering of the optical fiber component can be effected through chemical etching or physical abrasion. It is further understood that the physical abrasion can be accomplished by using a gritty surface such as sand paper to longitudinally abrade the surface of the optical fiber component whether such is carried out in a distally tapering or a right-cylindrical pattern.

To further achieve a greater degree of light illumination uniformity, in accordance with the invention, highly reflective material or particles 25a, 25b, 25c, 25d respectively, are compounded with the inner member 17, fluid material 20, porous balloon member 18, and/or microporous membrane 30. As the light encounters the highly reflective material 25a–25d, it reflects in different directions producing a uniform glow. This addition of the highly reflective particles results in a scattering and dispersing of the light, thereby uniformly lighting the cylindrical elongated light-emanating area 28.

In the first embodiment as illustrated in FIG. 2, reflective material 25a is in the form of particles compounded with the inner tubular member 17 such that light passing through the inner tubular member will be reflected by the reflective particles 25a. Either these particles can be loaded into the polymer such as at extrusion of the inner member 17, or they can be coated onto one or both of the surfaces of the tubular member. Suitable reflective material includes titanium dioxide ($TiO_2$) and silver, with titanium dioxide being preferred. The presence of the reflective material causes the light emanating from the optical fiber to reflect and disperse at least along the entire length of the light-emanating area 28, producing a uniform cylindrically-shaped ring of illumination that delivers the light energy uniformly along the length of the vessel or the like at which the photodynamic treatment fluid is located. The uniform light has the desirable effect of eliminating light energy "hot spots" and uneven activation of the treatment fluid.

The second embodiment of the present invention, illustrated in FIG. 3, calls for the presence of the reflective material 25b the fluid material 20. Reflective material 25b is in the form of particulates suspended within the fluid material 20, resulting in the reflection off of these particles of the light emanating from the optical fiber 16. It will be noted that the thus reflective fluid filled within the annular chamber 21 fully surrounds the light-emanating area and provides a depth of reflective particles in the fluid through which the light must pass along its path to the balloon 18 and hence to the vessel wall. Reflection off the particles and the resulting light dispersion produces a uniform light having the previously mentioned desirable effects of eliminating the uneven activation of the treatment fluid which is generally along the outside surface of the balloon member 18.

The third embodiment, illustrated in FIG. 4, is generally similar to that of FIG. 2. In this embodiment the reflective material 25c in the nature of highly reflective particles compounded with the material of the porous balloon member 18, for example either coated on the porous balloon member 18 or loaded into the polymer out of which the porous balloon member 18 is constructed. It will be appreciated that the loading is accomplished during the extrusion of the parison from which porous balloon member 18 is subsequently formed. The presence of the reflective material produces a reflecting and scattering effect. The inner tubular member 17 and the fluid material 20 in this embodiment are light-passing in order to allow light transmission from the optical fiber 16. As the light encounters the porous balloon member 18, the reflective particles 25c integrate the light along at least the treatment length and transmit a portion of the light energy to the vessel wall to be treated. This allows the light to be more uniform and even as it is transmitted through the porous balloon member 18 wall creating an even distribution of light energy to activate the treatment fluid 23 (photodynamic substance) already infused in or otherwise dispersed to the vessel wall, especially to the diseased area 22.

A fourth embodiment is illustrated in FIG. 5. In this embodiment the reflective material 25d is in the nature of highly reflective particles compounded with the material of the microporous membrane 30, for example either coated on the surface of the microporous membrane 30 or loaded into the polymer out of which the microporous membrane 30 is constructed. The highly reflective material 25d can be titanium dioxide ($TiO_2$), silver (Ag), aluminum (Al), or aluminum dioxide ($AlO_2$). In this embodiment the preferred reflective material is aluminum dioxide. It will be appreciated that the loading is accomplished during the extrusion of the parison from which microporous membrane 30 is subsequently formed. The presence of the reflective material produces a reflecting and scattering effect. The inner tubular member 17, the fluid material 20, and the porous balloon member 18 in this embodiment are light-passing in order to allow light transmission from the optical fiber 16. As the light encounters the microporous membrane 30, the reflective particles 25d integrate the light along at least the treatment length and transmit a portion of the light energy to the vessel wall to be treated. This allows the light to be more uniform as it is transmitted through the microporous membrane 30 creating an even distribution of light energy to activate the treatment fluid 23 (photodynamic substance) already infused in or otherwise dispersed to the vessel wall.

Moreover, the density and the size of the micropores on the microporous membrane 30 determine the amount of the light energy transmitted or integrated before the illumination of the treatment fluid 23. When the reflective particles are compounded with the polymer out of which the inner tubular member, the balloon member, and/or microporous membrane are constructed, the amount of loading can be between about 5 and about 40 weight percent reflective material based on the total weight of the polymer. It is preferred that this ratio be in the range of about 10 to about 40 weight percent, most preferably between about 25 to about 35 by weight of the total weight of the polymer. An alternative approach for compounding the porous balloon member 18, inner member 17, or the microporous membrane 30 with reflective particles includes coextruding or otherwise positioning a layer of highly reflective material or particles between two layers of polymer. It has been noted that 90% light illumination uniformity can be achieved when compounding the fluid material 20, porous balloon member 18, and/or microporous membrane 30 with reflective material 25b, 25c, and 25d, respectively.

With more particular reference to the light dissipation achieved, especially in the third and fourth embodiments, light is integrated before it emanates from the porous balloon member 18 or microporous membrane 30 into the vessel wall. By rendering the porous balloon member 18 or microporous membrane 30 material semi-reflective and semi-transparent, one can achieve more uniformity along the cylindrical surface of the porous balloon member 18 or microporous membrane 30, thereby optimizing the delivery of light to the treatment fluid 23 which has been absorbed into the vessel wall to be treated. The microporous membrane 30 is a biocompatible polymer. The microporous membrane 30 is made of a biocompatible polymer, and typically can be made of polymers of the type used in manufacturing the inner member 17. Here, the preferred material for the microporous membrane 30 is aluminized polyethylene terephthalate.

In the above embodiments, coating of the inner member 17, porous balloon member 18 or microporous membrane 30 can be achieved by known methods such as evaporation, sputtering, or ion bombardment of the reflective material. Such coating can be on the inside, the outside or both the inside and outside of the inner member 17, porous balloon member 18, or microporous membrane 30.

In the present invention the reflective material can be included in any one or a plurality of the inner member 17, porous balloon member 18, fluid material 20 and microporous membrane 30 in any combination. By adding the reflective material in these different combinations, it is possible to tailor the reflectivity and uniformity of light illumination to fit a particular need or a criterion for activating any of various photodynamic medicaments and the like.

It will be understood that the embodiments of the present invention which have been described are illustrative of some of applications of the principles of the present invention. Various modifications may be made by those skilled in the art without departing from the true spirit and scope of the invention.

I claim:

1. A photodynamic therapy balloon catheter for activating treatment fluid at a location within a living body, the catheter comprising:

an elongated tubular assembly having a proximal portion which remains outside of the living body when in use, the assembly also having a distal portion which is inserted into the living body when in use;

an optical fiber extending along the length of said assembly, said optical fiber having a generally distal light energy emanating section;

said elongated tubular assembly having a light-passing inner tubular member cylindrically surrounding said optical fiber and extending longitudinally along the length of the light energy emanating section of said optical fiber;

a light-passing inflatable porous balloon member having a plurality of holes to permit treatment fluid to pass through said balloon member and positioned at said distal portion of the assembly, said balloon member being in fluid-passing communication with said proximal portion of the assembly, said balloon member cylindrically surrounding said inner tubular member and extending longitudinally with respect to said inner tubular member;

a light source communicating with said optical fiber to deliver light energy to said light energy emanating section; and a light-passing microporous membrane member having a plurality of micropores to permit treatment fluid to pass through said inner porous membrane and positioned over the outer surface of said inflatable porous balloon member; and at least one of said inner tubular member, said porous balloon member, and said microporous membrane member includes light-reflective material which upon light emanating through the light energy emanating section, reflects said light energy and activates photodynamic treatment fluid at a location within a living body.

2. The photodynamic therapy balloon catheter of claim 1, wherein said light-reflective material is present in a quantity so as to disperse the light energy and produce a uniform illumination of light.

3. The photodynamic therapy balloon catheter of claim 1, wherein said generally distal light energy emanating section extends longitudinally for a distance approximating the length of a cylindrical working surface of the balloon member.

4. The photodynamic catheter of claim 1, wherein said optical fiber is tapered such that said optical fiber decreases in thickness in the distal direction, wherein the light emanating from said light energy emanating section of said optical fiber is a uniformly illuminating light.

5. The photodynamic therapy balloon catheter of claim 1, wherein said inner tubular member is loaded with reflective material.

6. The photodynamic therapy balloon catheter of claim 1, wherein said inner tubular member is coated with reflective material.

7. The photodynamic therapy balloon catheter of claim 1, wherein said balloon member is loaded with said reflective material.

8. The photodynamic therapy balloon catheter of claim 1, wherein the balloon member is coextruded with reflective material such that said reflective material is positioned between an inner layer and an outer layer of said balloon member.

9. The photodynamic therapy balloon catheter of claim 1, wherein said balloon member is coated with reflective material.

10. The photodynamic therapy balloon catheter of claim 1, wherein said light-reflective material is $TiO_2$.

11. The photodynamic therapy balloon catheter of claim 1, wherein said microporous membrane member is coated on at least one surface thereof with said light-reflective material.

12. The photodynamic therapy balloon catheter of claim 1, wherein said microporous membrane member is loaded with said light-reflective material.

13. The photodynamic therapy balloon catheter of claim 1, wherein the light-reflective material is present at from about 5 to about 40 percent by weight of the total weight of the member within which it is included.

14. The photodynamic therapy balloon catheter of claim 13, wherein the light-reflective material is present at from about 10 to about 40 percent by weight.

15. The photodynamic therapy balloon catheter of claim 1, wherein the micropores of said membrane are from about 0.4 to about 3 microns in diameter, the holes of said balloon being from about 5 to about 100 microns in diameter.

16. The photodynamic therapy balloon catheter of claim 1, wherein the number of said micropores per square centimeter of said membrane is between about one hundred thousand and about five hundred million.

17. The photodynamic therapy balloon catheter of claim 1, wherein the number of said pores in the inflatable balloon member is from about 20 to about 1000.

18. A photodynamic therapy balloon catheter for activating treatment fluid to a location within a living body, the catheter comprising:

an elongated tubular assembly having a proximal portion which remains outside of the living body when in use, the assembly also having a distal portion which is inserted into the living body when in use;

an optical fiber extending along the length of said assembly, said optical fiber having a generally distal light energy emanating section;

said elongated tubular assembly having a light passing inner member cylindrically surrounding said optical fiber and extending longitudinally along the length of the light energy emanating section of said optical fiber;

a light-passing inflatable porous balloon member having a plurality of holes to permit treatment fluid to pass through said balloon member and positioned at said distal portion of the assembly, said balloon member being in fluid-passing communication with said proximal portion of the assembly, and said balloon member cylindrically surrounding said inner tubular member and extending longitudinally along the length of said inner tubular member;

a light-passing fluid material positioned between said inner member and said inflatable balloon member;

a light source communicating with said optical fiber to deliver light energy to said light energy emanating section;

a light-passing microporous membrane member having a plurality of micropores to permit treatment fluid to pass through said microporous membrane and positioned over the outer surface of said inflatable porous balloon member; and at least one of said inner member, said porous balloon member, said fluid material, and said microporous membrane member includes light-reflective material which upon light emanating through the light energy emanating section, reflects said light energy and activates photodynamic treatment fluid at a location within a living body.

19. The photodynamic catheter of claim 18, wherein said light-reflective material is present in a quantity so as to disperse the light energy and produce a uniform illumination of light.

20. The photodynamic therapy balloon catheter of claim 18, wherein said generally distal light energy emanating section extends longitudinally for a distance approximating the length of a cylindrical working surface of the balloon member.

21. The photodynamic catheter of claim 18, wherein said optical fiber is tapered such that said optical fiber decreases in thickness in the distal direction, wherein the light emanating from said light energy emanating section of said optical fiber is a uniformly illuminating light.

22. The photodynamic therapy balloon catheter of claim 18, wherein said inner member is loaded with reflective material.

23. The photodynamic therapy balloon catheter of claim 18, wherein said inner member is coated with reflective material.

24. The photodynamic therapy balloon catheter of claim 18, wherein said balloon member is loaded with reflective material.

25. The photodynamic therapy balloon catheter of claim 18, wherein the balloon member is coextruded with reflective material such that said reflective material is positioned between an inner layer and an outer layer of said balloon member.

26. The photodynamic therapy balloon catheter of claim 18, wherein said balloon member is coated with reflective material.

27. The photodynamic therapy balloon catheter of claim 18, wherein said light-reflective material is $TiO_2$.

28. The photodynamic therapy balloon catheter of claim 18, wherein said microporous membrane is coated on at least one surface thereof with said light-reflective material.

29. The photodynamic therapy balloon catheter of claim 18, wherein said microporous membrane is loaded with said light-reflective material.

30. The photodynamic therapy balloon catheter of claim 18, wherein the light-reflective material is present at from about 5 to about 40 percent by weight of the total weight of the member within which it is included.

31. The photodynamic therapy balloon catheter of claim 18 wherein the micropores of said membrane are from about 0.4 to about 3 microns in diameter, the holes of said balloon being essentially from about 5 to about 100 microns in diameter, the number of said micropores per square centimeter of said membrane is between about one hundred thousand and about five hundred million, and the number of said holes in the inflatable balloon member is essentially from about 20 to about 1000.

32. A method for activating treatment fluid at a location within a living body, the method comprising the steps of:

providing a photodynamic catheter for insertion into a living body, the catheter including an elongated tubular assembly having a proximal portion, a distal portion; an optical fiber having a generally distal light energy emanating section, a light-passing inner member cylindrically surrounding said optical fiber, a light- passing inflatable porous balloon member, a light-passing microporous membrane at said distal portion of the assembly; and a light source communicating with said optical fiber to deliver light energy to said light energy emanating section;

said providing step includes adding a supply of reflective material to at least one of said inner member, said porous balloon member, and said microporous membrane;

transluminally inserting the catheter to a location within the living body;

introducing a photodynamic treatment fluid through the photodynamic catheter and to the location within the living body;

transmitting light energy from said light source using the optical fiber through said light energy emanating section to the location within the body wherein the photodynamic treatment fluid is introduced;

activating the photodynamic treatment fluid in vivo by emanating light through the light energy emanating section, with the light reflecting from said reflective material, thereby illuminating and activating the photodynamic treatment fluid at said location within the living body; and withdrawing the catheter from the living body.

33. The method of claim 32, wherein the activating step further includes the step of uniformly dispersing the light.

34. The method of claim 33, wherein the step of uniformly dispersing the light further includes the step of reflecting said light from the reflective material added to said inner member.

35. The method of claim 33, wherein the step of uniformly dispersing the light further includes the step of reflecting said light from the reflective material added to said balloon member.

36. The method of claim 33, whereon the step of uniformly dispersing the light further includes the step of reflecting said light from the reflective material added to said microporous membrane.

37. The method of claim 32, wherein said treatment fluid is a photodynamic medicament.

38. The method of claim 32, further including the step of inflating the porous balloon member so as to contact the location within the living body.

39. The method of claim 38, wherein said step of inflating takes place after the step of introducing a treatment fluid and before the step of transmitting light energy.

40. A method for activating treatment fluid at a location within a living body, the method comprising the steps of:

providing a photodynamic catheter for insertion into a living body, the catheter including an elongated, tubular assembly having a proximal portion, a distal portion; an optical fiber having a generally distal light energy emanating section, a light-passing inner member cylindrically surrounding said optical fiber, a light- passing inflatable porous balloon member, a light-passing microporous membrane at said distal portion of the assembly; and a light source communicating with said optical fiber to deliver light energy to said light energy emanating section;

transluminally inserting the photodynamic catheter to a location within the living body;

introducing a photodynamic treatment fluid through the catheter to the location within the living body;

flowing a light-passing fluid material between said inner member and said inflatable porous balloon member, and wherein said fluid material includes light-reflective material;

transmitting light from said light source using the optical fiber through said light energy emanating section to the location within the body wherein the photodynamic treatment fluid is introduced;

activating the photodynamic treatment fluid by emanating light through the light energy emanating section, with the light reflecting from said reflective material, thereby illuminating and activating the photodynamic treatment fluid at said location within the living body; and withdrawing the catheter from the living body.

41. The method of claim 40, wherein said providing step further includes adding a supply of light-reflective material to at least one of said inner member, said porous balloon member, and said microporous membrane.

42. The method of claim 41, wherein the activating step further includes the step of uniformly dispersing the light.

43. The method of claim 42, wherein the step of uniformly dispersing the light further includes the step of reflecting said light from the reflective material added to at least one of said inner member, said porous balloon member, and said microporous membrane.

44. The method of claim 42, wherein the step of uniformly dispersing the light further includes the step of reflecting said light from the reflective material added to said fluid material.

* * * * *

UNITED STATES PATENT AND TRADEMARK OFFICE
CERTIFICATE OF CORRECTION

PATENT NO. : 5,709,653
DATED : January 20, 1998
INVENTOR(S) : James E. Leone

It is certified that error appears in the above-indentified patent and that said Letters Patent is hereby corrected as shown below:

On the Cover Sheet, under FOREIGN PATENT DOCUMENTS, for Patent
   No. 2154761, replace "Georgia" with --Great Britain--.
Col. 1, line 14, "in vivo" should be in italics.
Col. 4, line 32, "typically, from" should read --typically from--.
Col. 6, line 16, "25b the" should read --25b in the--; line 31,
   "25c in" should read --25c is in--.
Col. 7, line 20, "35 by" should read --35 percent by--; line 67,
   "of applications" should read --applications--.
Col. 11, line 20, "in vivo" should be in italics.

Signed and Sealed this

Twenty-fourth Day of November,1998

Attest:

BRUCE LEHMAN

Attesting Officer

Commissioner of Patents and Trademarks